United States Patent [19]

Grill et al.

[11] Patent Number: 4,725,670
[45] Date of Patent: Feb. 16, 1988

[54] HIGH-CYSTEINE PEPTIDES WITH ALPHA-GLUTAMIC ACID UNITS, PROCESS FOR THEIR PRODUCTION AND APPLICATION OF SAME

[75] Inventors: Erwin Grill; Ernst-Ludwig Winnacker; Meinhart H. Zenk, all of Munich, Fed. Rep. of Germany

[73] Assignee: Consortium für Elektrochemische Industrie GmbH, Munich, Fed. Rep. of Germany

[21] Appl. No.: 829,317

[22] Filed: Feb. 14, 1986

[30] Foreign Application Priority Data

Mar. 1, 1985 [DE] Fed. Rep. of Germany ....... 3507315
Aug. 19, 1985 [DE] Fed. Rep. of Germany ....... 3529625

[51] Int. Cl.⁴ .......................... C07K 7/08; C07K 7/06; C07K 7/02
[52] U.S. Cl. ................................... 530/326; 530/327; 530/328; 530/332
[58] Field of Search ................ 530/326, 327, 328, 332

[56] References Cited

PUBLICATIONS

Chem. Abstr., vol. 103, (1985), 71658.
Tetrahedron Letters, vol. 25, No. 35, 3869–3872.

*Primary Examiner*—Delbert R. Phillips
*Attorney, Agent, or Firm*—Collard, Roe & Galgano

[57] ABSTRACT

A high-cysteine polypeptide having an amino acid sequence of the formula:

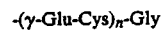

-(γ-Glu-Cys)$_n$-Gly in which,
n is an integer from 4 to 7,
γ-Glu represents γ-glutamic acid,
Cys represents cysteine, and
Gly represents glycine, for use in pharmaceutical preparations for treating acute and chronic heavy metal poisoning. Alternatively, the polypeptides may be employed in the treatment of metal deficiency phenomena or for maintaining the homeostasis in physiological systems with respect to such metals as iron or zinc. Processes for producing the polypeptides of the invention are also disclosed.

4 Claims, No Drawings

HIGH-CYSTEINE PEPTIDES WITH ALPHA-GLUTAMIC ACID UNITS, PROCESS FOR THEIR PRODUCTION AND APPLICATION OF SAME

This invention relates to high-cysteine peptides having γ-glutamic acid units or segments.

Proteins having a relatively high proportion of the amino acid cysteine that are of animal origin (metallo-thioneines) are known. The amino acids of these proteins are linked with one another by α-peptide bonds. Such metallo-thioneines are capable of bonding considerable amounts of heavy metal and are assumed to serve a detoxification or decontamination function in organisms loaded with such heavy metals (see in this regard Kägi, *J. Biochem.* 89, 1839, (1981)).

Furthermore, peptides of the formulas:

H-γGlu-Cys-γ-Glu-Cys-Gly-OH and

H-γGlu-Cys-γ-Glu-Cys-γ-Glu-Cys-Gly-OH, which are obtained from the breakdown of yeasts, are known from *Agric. Biol. Chem.* 49, 71, (1985).

An object of the present invention is to provide peptides, hereinafter also referred to as phytochelatines, which are characterized by the following amino acid sequence:

-(γ-Glu-Cys)$_n$-Gly-, wherein n is an integer from 4 to 7; γ-Glu represents γ-glutamic acid; Cys represents cysteine; and Gly is glycine.

The peptide segments according to the invention may be described by the following structural formulas:
n=4: γGlu-Cys-γ-Glu-Cys-γ-Glu-Cys-γ-Glu-Cys-Gly
n=5: γGlu-Cys-γ-Glu-Cys-γ-Glu-Cys-γ-Glu-Cys-γ-Glu-Cys-Gly
n=6: γGlu-Cys-γ-Glu-Cys-γ-Glu-Cys-γ-Glu-Cys-γ-Glu-Cys-γ-Glu-Cys-Gly
n=7: γGlu-Cys-γ-Glu-Cys-γ-Glu-Cys-γ-Glu-Cys-γ-Glu-Cys-γ-Glu-Cys-γ-Glu-Cys-Gly A further object of the present invention is to provide phytochelatines with a content of metal cations. Basically, this includes all metal cations capable of entering into a coordinative bond with the thiolate groups of the corresponding phytochelatine. Examples are, in particular, the cations of the metals lead, tin, bismuth, titanium, vanadium, molybdenum, manganese, cobalt, nickel, iron, copper, silver, gold, platinum, palladium, zinc, cadmium, mercury, uranium, arsenic and selenium.

Naturally, the metal content is dependent upon the valency of the cation coordinatively bonded to the thiolate groups. The metal content amounts to from 1 to 4 moles; with bivalent cations, the metal content is normally 2 moles per mole phytochelatine.

The phytochelatines, according to the present invention, are able to be obtained by extracting plant material. Basically, the plant material includes both the lower and higher plants. Preferably, however, the angiosperms and, in particular, the dicotylic angiosperms are used, the latter because of their easy accessibility.

The following plant material is specified, by way of example, for obtaining the phytochelatines:

Plant material from the family of Apocynaceae, in particular *Catharantus roseus*, *Rauwolfia serpentina*, *Rhazya stricta;* from the family of Berberidaceae, in particular, *Berberis stolonifera;* from the family of Brassicaceae, in particular, *Thlaspi alpestre;* from the family of Caryophyllaceae, in particular, *Silene cucubalus;* from the family of Papaveraceae, in particular, *Fumaria parviflora;* from the family of Ranunculaceae, in particular, *Thalictrum dipterocarpum;* from the family of Rubiaceae, in particular, *Galium mollugo;* from the family of Rosaceae, in particular, *Rosa canina* and *Malus silvestris;* from the family of Solanaceae, in particular, *Solanum marginatum* and *Nicotiana rustica;* from the family of Asteraceae, in particular, *Echinacea purpurea;* and from the family of Apiaceae, in particular, *Anethium graveoleus.*

Preferably, cell cultures of these plants are used as the plant material. However, the differentiated plants or parts of plants may also be used for obtaining the peptides of the invention.

The formation of the phytochelatines in the plants is induced by treating the plants with at least one metal or metal salt. This treatment may be carried out in a suitable manner in which the plants are capable of absorbing the metals or metal cations. Preferably, the formation of the phytochelatines is induced by treating cell cultures with metal salt solutions in an aqueous system. Typically, the procedure is as follows: The cell material is cultivated in the metal salt solution, whereby metal concentrations are maintained which are below the acute phytotoxicity. The lower limit of the metal concentration is approximately 1 μmole per liter. As mentioned above, the upper limit is highly dependent upon the phytotoxicity of the metal cation involved; the metal concentration may range up to 100 mmoles per liter. Preferably, the metal concentration is the range of 10 μmoles per liter to 1 mmole per liter.

Hence, for obtaining the phytochelatines, the use of plant material that has been cultivated in the presence of metals or metal cations is the preferred mode.

The plant material is extracted by using those methods which permit the extraction of peptides from plants. Typically, a procedure is used by which the cell structure of the plants or the cell cultures are destroyed. With such a procedure, the plant material is advantageously frozen, for example, with liquid nitrogen, crushed, if necessary, and, finally, incorporated in an aqueous, slightly alkaline preparation. It is most useful if the pH of the aqueous preparation is in the range of 7.5-9.5. However, acid preparations with a pH of from 1-3 may also be used. Often, buffer solutions which are suitable for the particular pH ranges are used as the aqueous preparations.

After separating plant material that was not decomposed, if any, the extract is further treated. It is most useful if the extract is first concentrated, which may be achieved, for example, by freeze-drying or by absorption of the peptides on an ion-exchanger and subsequent eluating.

Thereafter, the co-extracted proteins are precipitated by adding an electrolyte, for example, an ammonium sulfate solution. The peptides, according to the present invention, remain in solution during the precipitation step. Finally, additional purification steps may follow, for example, ultra-filtration, gel filtration or precipitation of the phytochelatines with a copper sulfate solution. In each case, the eluates may be selected based on UV-measurements in accordance with the typical absorption bands for the metal-thiolate bond as well as, if need be, by qualitative detection of the SH-functions (for example, with Ellman's Reagent).

If the plant material was incorporated or received in a basic medium, the phytochelatines are produced with a corresponding content of metal ions. The free peptides may be obtained, for example, by acidifying and precipitating (e.g., H$_2$S-precipitation) the metal cations. Alternatively, the metal cation-loaded peptides may be relieved of the metal content, for example, with the aid of complexing agents (e.g., ethylene diamine tetraacetate).

If the plant material is incorporated in acid preparations, the peptides are obtained without a metal cation content.

As a general rule, the peptides of the present invention of the formula

$$NH_3^+\text{-}(\gamma\text{-Glu-Cys})_n\text{-Gly-COO}^-$$

are obtained as mixtures, whereby the peptide

$$NH_3^+\text{-}(\gamma\text{-Glu-Cys})_4\text{-Gly-COO}^-$$

is the principal component among the peptides according to the invention. In most cases, the frequency of this segment comes to from 3 to 8 times the amount of the higher chain peptides.

The typical frequency distribution of the peptide segments as a percentage of the peptide mixture, based on the total amount of peptides according to the invention, can be derived from the following data:

70–90 mole-% ($\gamma$-Glu-Cys)$_4$-Gly

5–15 mole-% ($\gamma$-Glu-Cys)$_5$-Gly

2–10 mole-% ($\gamma$-Glu-Cys)$_6$-Gly 0.1–5 mole-% ($\gamma$-Glu-Cys)$_7$-Gly

Furthermore, the mixtures may contain analogous short-chain peptides, in particular, ($\gamma$-Glu-Cys)$_3$-Gly and ($\gamma$-Glu-Cys)$_2$-Gly, which is not taken into account in the above mole percentage data.

If desired, the peptides may be separated by currently known methods. Such methods include, for example, high pressure liquid chromatography ("HPLC"), gel filtration, chromatography or ion-exchangers, among other techniques.

The inventive peptides may be used individually, in mixture (i.e., as substances) or in the form of preparations of the type which have been used for formulating peptide compositions. For example, via known techniques, the peptides according to the invention may be adsorbed, physically or chemically, on carrier materials. Examples of such carrier materials include alginates, agaroses having functional groups (such as, e.g., the oxirane group), cellulose, polyacrylic resins, glasses, silicates, among others.

The peptides according to the invention find use in the form of pharmaceutical preparations for treating acute and chronic heavy metal poisoning. Alternatively, the inventive peptides, which are loaded with metal cations, may also be used for the treatment of metal deficiency phenomena or for maintaining the homeostasis of the corresponding metals (e.g., iron, zinc).

Other applications exist in the field of environmental protection, for example, the treatment of waste water polluted with heavy metals.

Additionally, the peptides according to the invention may be used for enriching valuable metals from aqueous solutions.

In addition, peptides of the invention, which are loaded with heavy metals, may be used for obtaining the corresponding antibodies, which in turn serve as a diagnostic agent for determining the degree to which plants are loaded with heavy metals.

The invention will now be explained more fully in a number of examples which are, however, only given by way of illustration and not of limitation.

EXAMPLE 1

1,000 g (conforming to 33 g dry weight) of a cell culture of *Rauwolfia serpentina* was cultivated for 5 days under constant shaking in 3 liters of a 300 $\mu$molar aqueous cadmium sulfate solution. Subsequently, the cell culture was harvested, washed with distilled water and frozen in liquid nitrogen. Thereafter, the cell culture having been broken down was suspended in 500 ml buffer solution (10 mmolar aqueous solution of trihydroxylmethylamino methane/HCl/2-mercaptoethanol) with a pH of 8.6.

The suspension was then centrifuged. The supernatant layer was again adjusted to a pH of 8.6 and diluted so that the conductivity came to <1 kS. Thereafter, the supernatant layer was passed through an anion exchanger column (diethylaminoethyl-agarose column).

Subsequently, eluating was carried out with an aqueous solution (0.5 moles/l NaCl; 10 mmoles/l trihydroxylmethylaminomethane/HCl; pH=8.6). For precipitating the protein, solid ammonium sulfate was added to the eluate until the saturation level reached 85%. Thereafter, the mixture was centrifuged and the supernatant layer was relieved of ammonium sulfate by ultra-filtration and then concentrated to 15 ml.

Finally, the concentrated solution was subjected to gel filtration (Sephadex ®G-50, Pharmacia Company, Uppsala, Sweden) at a pH of 7. The pH was adjusted accordingly with ammonium acetate. By eluating with 5 mmolar ammonium acetate solution, a small proportion of high-molecular protein was initially obtained followed by the desired peptides.

After lyophilizing the eluate, 200 mg peptide mixture was obtained; the cadmium content came to 15.7% by weight.

EXAMPLE 2

100 mg of the peptide mixture obtained in accordance with Example 1 was dissolved in 2 ml of 0.01N hydrochloric acid. Gaseous hydrogen sulfide was admitted into the solution resulting in precipitation of cadmium sulfide. Subsequently, centrifugation was carried out and the supernatant layer was lyophilized. 84 mg of a metal-free peptide mixture was obtained.

The peptide mixture was separated by HPLC on a "reversed phase" column (Nucleosil C - 18, 10 $\mu$m, Macherey & Nagel, Düren, Fed. Rep. of Germany). The mixture had the following composition:

44.9 mole-% $NH_3^+$-($\gamma$-Glu-Cys)$_3$-Gly-$COO^-$ 47.6 mole-% $NH_3^+$-($\gamma$-Glu-Cys)$_4$-Gly-$COO^-$ 5.6 mole-% $NH_3^+$-($\gamma$-Glu-Cys)$_5$-Gly-$COO^-$ 1.7 mole-% $NH_3^+$-($\gamma$-Glu-Cys)$_6$-Gly-$COO^-$ 0.1 mole-% $NH_3^+$-($\gamma$-Glu-Cys)$_7$-Gly-$COO^-$ 0.1 mole-% account for rounding error

EXAMPLE 3

50 mg of the metal-free peptide mixture (according to Example 2) was dissolved in 2 ml 0.01N hydrochloric acid and mixed with 250 μmoles of iron sulfate in the form of a 1 molar solution. This mixing step was carried out in a nitrogen atmosphere. Subsequently, the mixture was neutralized with 0.01N soda lye (pH=7.5). The solution so obtained was finally loaded in an agarose column (Sephadex ®G-25, Pharmacia Company, Uppsala, Sweden). After eluating with water and lyophilizing of the eluate, an iron-loaded peptide mixture was obtained with a yield of 50 mg.

While only several embodiments and examples of the present invention have been described, it is obvious that many changes and modifications may be made thereunto, without departing from the spirit and scope of the invention.

What is claimed is:

1. A polypeptide chain, comprising an amino acid sequence of the formula:

$$\text{-}(\gamma\text{-Glu-Cys})_n\text{-Gly}$$

wherein,
n is an integer from 4 to 7,
$\gamma$-Glu represents $\gamma$-glutamic acid,
Cys represents cysteine, and
Gly represents glycine.

2. The polypeptide chain according to claim 1, further comprising a content of metal cations capable of entering into a coordinative bond with a thiolate group of said polypeptide.

3. The polypeptide chain according to claim 2, wherein said content of metal cations is from 1 to 4 moles per mole of said polypeptide chain.

4. The polypeptide chain according to claim 2, wherein said content of metal cations includes a member selected from the group consisting of lead, tin, bismuth, titanium, vanadium, molybdenum, manganese, cobalt, nickel, iron, copper, silver, gold, platinum, palladium, zinc, cadmium, mercury, uranium, arsenic, selenium and a combination thereof.

* * * * *